US008886277B2

(12) United States Patent
Kim et al.

(10) Patent No.: US 8,886,277 B2
(45) Date of Patent: Nov. 11, 2014

(54) MICRO-ELECTRODE ARRAY PACKAGE USING LIQUID CRYSTAL POLYMER AND MANUFACTURING METHOD THEREOF

(75) Inventors: Sung June Kim, Seoul (KR); Seung Woo Lee, Gwacheon-si (KR); Choong Jae Lee, Seoul (KR); Soonkwan An, Seoul (KR)

(73) Assignees: SNU R&DB Foundation, Seoul (KR); M.I.Tech Co., Ltd, Pyeongtaek-si (KR)

( * ) Notice: Subject to any disclaimer, the term of this patent is extended or adjusted under 35 U.S.C. 154(b) by 343 days.

(21) Appl. No.: 13/143,538

(22) PCT Filed: Aug. 14, 2009

(86) PCT No.: PCT/KR2009/004558
§ 371 (c)(1),
(2), (4) Date: Aug. 15, 2011

(87) PCT Pub. No.: WO2010/079875
PCT Pub. Date: Jul. 15, 2010

(65) Prior Publication Data
US 2011/0313269 A1    Dec. 22, 2011

(30) Foreign Application Priority Data

Jan. 7, 2009 (KR) .......................... 10-2009-0001282

(51) Int. Cl.
*A61B 5/04* (2006.01)
*A61N 1/05* (2006.01)
(Continued)

(52) U.S. Cl.
CPC ............ *H01L 21/56* (2013.01); *A61B 5/04001* (2013.01); *A61B 5/6877* (2013.01); *H01L*
(Continued)

(58) Field of Classification Search
CPC ........ A61B 5/04; A61B 5/686; A61B 5/6867; A61B 2560/0406; A61B 2560/0412; A61B 2562/028; A61B 2562/12; A61B 2562/125; A61B 2562/166; A61B 2562/187; A61B 2562/227; A61N 1/0543; A61N 1/0551; A61N 1/36; A61N 1/36046; A61N 1/3605; A61N 1/37205; A61N 1/375–1/3758

USPC ................ 600/372, 393, 544–546, 373–381; 607/115–138; 29/825
See application file for complete search history.

(56) References Cited

U.S. PATENT DOCUMENTS
6,372,992 B1    4/2002 Yang
(Continued)

FOREIGN PATENT DOCUMENTS
JP         07-162258         6/1995
(Continued)

OTHER PUBLICATIONS
Zou et al. "Characterization of Liquid Crystal Polymer for High Frequency System-in-a-Package Applications" IEEE Trans. Advanced Packaging 25(4), pp. 503-508 (Nov. 2002).*
(Continued)

*Primary Examiner* — Lee S Cohen
*Assistant Examiner* — Erin M Cardinal
(74) *Attorney, Agent, or Firm* — Fenwick & West LLP

(57) ABSTRACT

Disclosed herein is a micro-electrode array package including a micro-electrode array comprising: a substrate section including a liquid crystal polymer; an electrode section collecting and transferring bio-signals; and a cover section insulating and protecting the electrode section and including a liquid crystal polymer, wherein the electrode section is disposed in contact with one surface of the substrate section, the cover section is adhered in contact with the surface of the substrate section on which the electrode section is disposed, and a space independent from the external environment is formed between the substrate section and the cover section adhered thereto. Disclosed herein too is a method for manufacturing a micro-electrode array package, including: forming alignment holes in a substrate section including a liquid crystal polymer and a cover section including a liquid crystal polymer; forming site window holes for an electrode section-exposure in the cover section; forming an electrode section on one surface of the substrate section; aligning the substrate section and the cover section by the alignment holes, and adhering the substrate section and the cover section with each other; and cutting the substrate section and the cover section adhered thereto to provide an outer shape.

8 Claims, 6 Drawing Sheets

(51) Int. Cl.
*H01L 21/56* (2006.01)
*A61B 5/00* (2006.01)
*H01L 23/31* (2006.01)
*H01L 23/498* (2006.01)
*H01L 23/48* (2006.01)
*H01L 23/66* (2006.01)

(52) U.S. Cl.
CPC .................. 23/3135 (2013.01); *H01L 23/49894* (2013.01); *A61B 2562/0209* (2013.01); *A61B 2562/046* (2013.01); *A61B 2562/125* (2013.01); *H01L 23/48* (2013.01); *H01L 23/66* (2013.01); *H01L 2223/6677* (2013.01); *H01L 2924/0002* (2013.01)
USPC .............................. 600/373; 29/825; 607/116

(56) References Cited

U.S. PATENT DOCUMENTS

| | | | | |
|---|---|---|---|---|
| 7,236,829 | B1* | 6/2007 | Farazi et al. | 607/36 |
| 7,301,108 | B2* | 11/2007 | Egitto et al. | 174/262 |
| 7,501,301 | B2 | 3/2009 | Kovacs et al. | |
| 2002/0198582 | A1* | 12/2002 | Edell et al. | 607/116 |
| 2004/0182509 | A1* | 9/2004 | Farquhar et al. | 156/250 |
| 2006/0057771 | A1 | 3/2006 | Kovacs et al. | |
| 2006/0212075 | A1* | 9/2006 | Marnfeldt | 607/2 |
| 2007/0055336 | A1* | 3/2007 | Greenberg et al. | 607/141 |
| 2008/0033500 | A1* | 2/2008 | Strother et al. | 607/36 |
| 2008/0051848 | A1 | 2/2008 | Greenberg et al. | |
| 2008/0275326 | A1* | 11/2008 | Kasielke et al. | 600/373 |
| 2008/0288037 | A1 | 11/2008 | Neysmith et al. | |
| 2008/0303022 | A1 | 12/2008 | Tai et al. | |
| 2010/0331933 | A1* | 12/2010 | Carbunaru et al. | 607/116 |
| 2011/0237921 | A1* | 9/2011 | Askin et al. | 600/377 |

FOREIGN PATENT DOCUMENTS

| | | |
|---|---|---|
| JP | 2008-525121 A | 7/2008 |
| KR | 10-0552115 B1 | 2/2006 |
| KR | 10-2008-0108897 A | 12/2008 |

OTHER PUBLICATIONS

Wang et al. "Liquid Crystal Polymer (LCP) for MEMS: Processes and Applications" J. Micromech. Microeng. 13, pp. 628-633 (2003).*

Lee et al. "Development of Microelectrode Arrays for Artificial Retinal Implants Using Liquid Crystal Polymers" Investigative Opthalmogy & Visual Science. 50(12), pp. 5859-5866 (Dec. 2009).*

Dupont Plastics, "Zenite® LCP . . . Succeeds when other plastics fall short" from www.plastics.dupont.com Oct. 2004, (retrieved via WayBack Machine Internet Archive Mar. 2014).*

PCT International Search Report and Written Opinion, PCT/KR2009/004558, Mar. 31, 2010, 10 Pages.

Canadian Intellectual Property Office, Office Action, Canadian Patent Application No. 2,751,307, Jul. 7, 2014, five pages.

* cited by examiner

MICRO-ELECTRODE ARRAY PACKAGE USING LIQUID CRYSTAL POLYMER AND MANUFACTURING METHOD THEREOF

TECHNICAL FIELD

This disclosure relates to a micro-electrode array package using a liquid crystal polymer and a method for manufacturing the same. More particularly, this disclosure relates to a micro-electrode array package that allows electrodes and signal processing and communication modules required for realizing sensors and neural prosthetics to be used for a long time while not being affected by moisture and ions in vivo, and to a method for manufacturing the same.

BACKGROUND ART

In general, the term 'micro-electrode array' refers to a structure attached to or implanted into a living body to convert bio-chemical responses and bio-signals into electric signals to be collected, or to deliver electric signals for neural stimulation.

The technology of micro-electrode array package disclosed herein includes bio-signal recording and stimulating electrodes (also referred to as 'micro-electrodes' hereinafter) and encapsulated packages thereof. Particularly, since the bio-signal recording and stimulating electrodes should be implanted into living bodies for a long time, they have to be electrically insulated and protected from being damaged by moisture and ions in vivo. Conventional micro-electrodes using polymers such as polyimide and parylene are susceptible to the in vivo environment, and thus are limited in their applications. Under these circumstances, liquid crystal polymers (also referred to as 'LCP' hereinafter) capable of resisting against the in vivo environment have been used as micro-electrode materials. However, because such LCPs have poor processability, there is an imminent need for a novel method.

Encapsulated packages are required for insulating and protecting bio-signal recording and neural stimulation devices or other electronic parts from moisture or ions. Since encapsulated packages should not adversely affect user's daily life after they are inserted into the user's body, one of the most important factors to be considered in designing the encapsulated packages is dimension. Therefore, there has been a need for packages that allow easy modification of dimensions and are strongly resistant against moisture or ions.

DISCLOSURE OF INVENTION

Technical Problem

Provided is a micro-electrode array package using a LCP that solves the above-mentioned problems in the related art. A method for manufacturing the micro-electrode array package is also provided.

Solution to Problem

Disclosed herein is a micro-electrode array package including a micro-electrode array comprising: a substrate section including LCP; an electrode section collecting and transferring bio-signals; and a cover section insulating and protecting the electrode section and including LCP, wherein the electrode section is disposed in contact with one surface of the substrate section, the cover section is adhered in contact with the surface of the substrate section on which the electrode section is disposed, and a space independent from the external environment is formed between the substrate section and the cover section adhered thereto.

Disclosed herein too is a method for manufacturing a micro-electrode array package, including: forming alignment holes in a substrate section including LCP and a cover section including LCP; forming site window holes for an electrode section-exposure in the cover section; forming an electrode section on one surface of the substrate section; aligning the substrate section and the cover section by the alignment holes, and adhering the substrate section and the cover section with each other; and cutting the substrate section and the cover section adhered thereto to provide an outer shape.

Advantageous Effects of Invention

The method disclosed herein enables manufacture of a micro-electrode array package in a stable and prompt manner. On the contrary, the processes of the related art have disadvantages in that they include long-term plasma etching operations, thereby causing damages on electrode patterns formed of metals, and are not time-efficient. In addition, the method disclosed herein avoids a need for forming an etching mask pattern and plasma etching operation, and thus reduces the time required for manufacturing micro-electrode array packages. Further, the method disclosed herein uses a single material for encapsulating micro-electrodes and other sections so that the assembled sections are not exposed to the exterior, and thus may be advantageous to achieve high-density multi-channel systems.

BRIEF DESCRIPTION OF DRAWINGS

The above and other aspects, features and advantages of the disclosed exemplary embodiments will be more apparent from the following detailed description taken in conjunction with the accompanying drawings in which.

MODE FOR THE INVENTION

Figure 1:
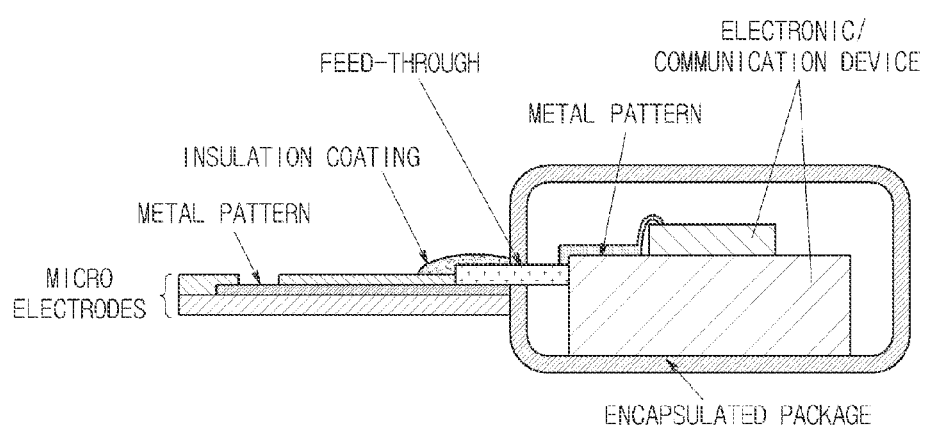
FIG. 1 is a sectional view showing a micro-electrode array package according to the related art.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

FIG. 1 is a sectional view showing a micro-electrode array package according to the related art. As shown in FIG. 1, according to the related art, an encapsulated package having electronic devices such as signal processing and communication units (referred to also as an "internal unit" hereinafter) enclosed therein is connected with a micro-electrode by way of a feed-through. The package is formed using a metal or ceramic material, and an exposed part of the feed-through is coated with an additional insulation material to prevent the feed-through from being exposed to the exterior. Thus, the micro-electrode array package according to the related art has poor sealability due to the heterogeneous binding between the encapsulated package and the micro-electrode, and thus is limited in electrodes channel extension.

Figure 2:
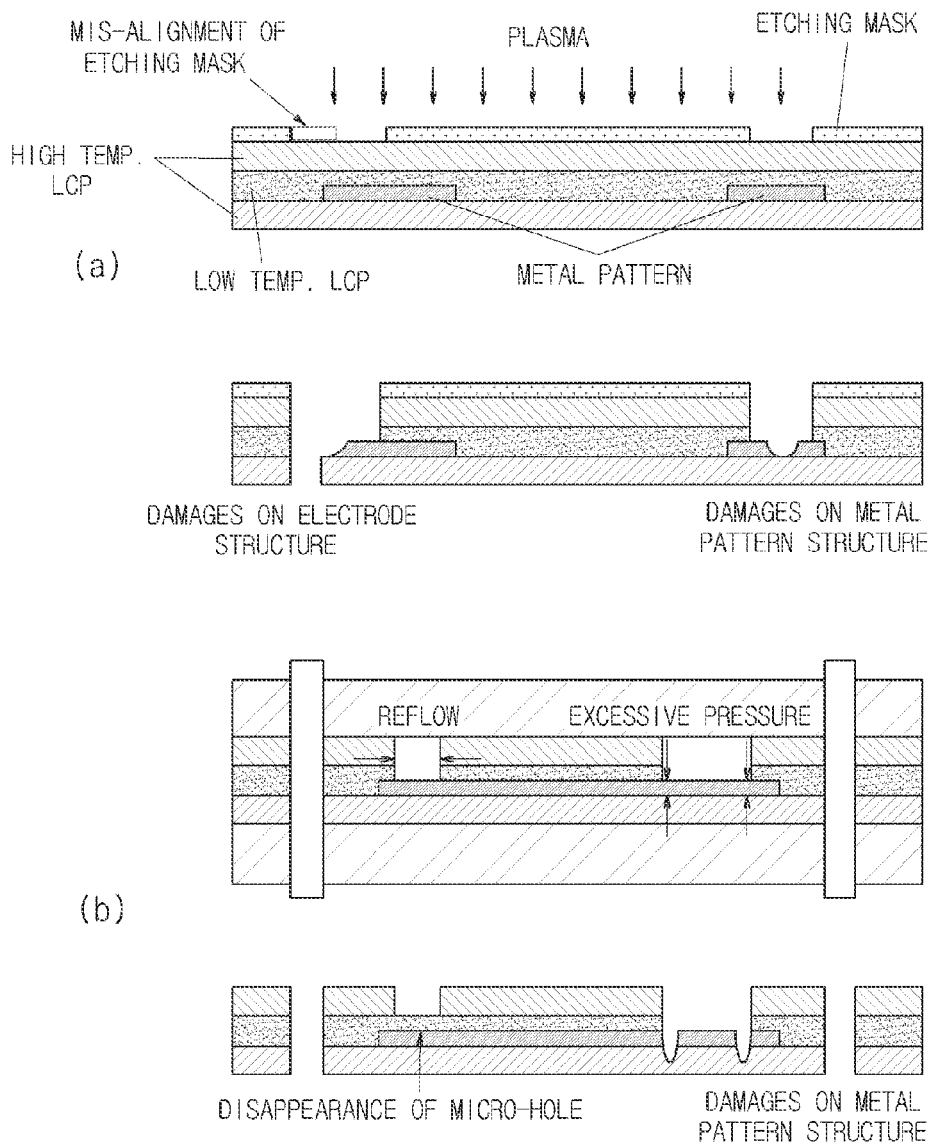
FIG. 2 illustrates a method for manufacturing a micro-electrode array using a LCP according to the related art.

FIG. 2 illustrates a method for manufacturing a micro-electrode array using a LCP according to the related art, wherein FIG. 2(a) shows a plasma etching process, and FIG. 2(b) shows a thermal-bonding process using a heat press.

Referring to FIG. 2(a), since the LCP is an opaque material, alignment keys on each layer cannot be seen through the LCP. In addition, after carrying out a thermal-bonding process by a heat press, the internal metal pattern is displaced due to the shrinkage and expansion of the LCP. Therefore, the method for manufacturing a micro-electrode according to the related art may cause misalignment of an etching mask, resulting in damages on the metal pattern or other structural parts. Further, the LCP has a low plasma etching rate and provides a non-uniformly etched surface. As a result, the plasma etching process according to the related art may cause damages on the metal pattern and other structural parts when forming the window holes for an electrode-exposure and the outer shape of electrode via plasma etching.

FIG. 2(b) illustrates an alternative process that avoids the above-mentioned problems of the plasma etching process as shown in FIG. 2(a). In the process as shown in FIG. 2(b), the window holes for an electrode-exposure are formed before carrying out the LCP bonding process. However, the process as shown in FIG. 2(b) entails another problem. In other words, during the thermal-bonding process by the heat press according to the related art, the same amount of pressure is applied to each layer, while the layer having the window holes therein is subjected to a relatively excessive amount of pressure at the border portion of the window holes. Such excessive pressure may cause damages on the metal pattern and other structural parts. Moreover, when the LCP has a lower melting point than the heating temperature of the heat press, a reflow phenomenon may occur, resulting in disappearance of the preformed micro-hole.

Figure 3:
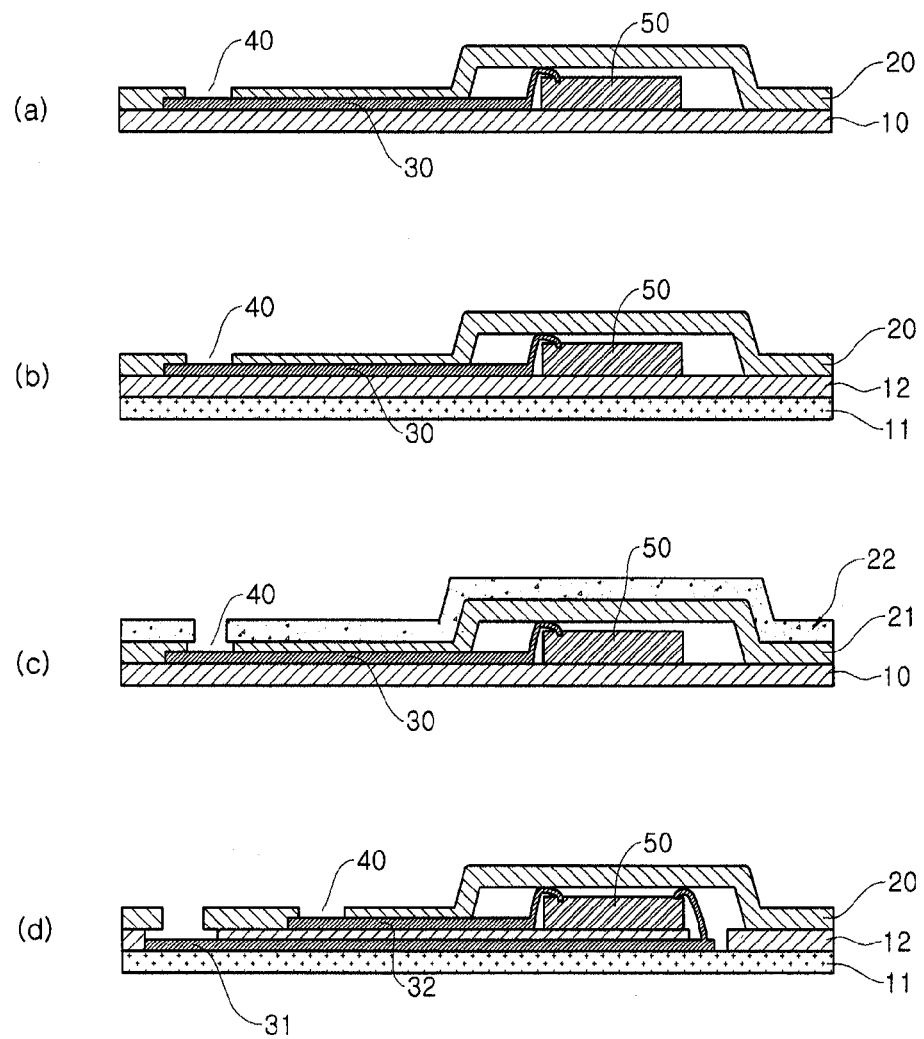
FIG. 3 is a sectional view showing the micro-electrode array package according to one embodiment disclosed herein.

FIG. 3 is a sectional view showing the micro-electrode array package according to one embodiment disclosed herein. The micro-electrode array package according to one embodiment disclose herein, is provided to overcome the above-mentioned problems occurring in the conventional processes of the related art as shown in FIG. 1 and FIG. 2. FIG. 3(a) shows a bi-layer structure, and FIG. 3(b), FIG. 3(c) and FIG. 3(d) each show a tri-layer structure. These multilayer structures could be utilized to control the overall height and surface curvature of the micro-electrode array package using several kinds of LCPs which have different thicknesses and coefficients of thermal expansion (CTE). In addition, the multi-layer structure as shown in FIG. 3(d) allows vertical extension of the number of channels by overcoming a limitation in the horizontal dimension of the package.

The micro-electrode array package as shown in FIG. 3(a) includes: a substrate section 10 including LCP; an electrode section 30 formed on the substrate layer; a functioning section 50 connected with the electrode section and carrying out signal processing and communication; and a cover section 20 insulating and protecting the electrode section and the functioning section and including LCP. The cover section further includes site window holes 40 through which the electrode section is exposed to the external environment. Bio-signals may be collected through the window holes 40, and then transferred to the functioning section 50 by way of the electrode section 30. In addition, the functioning section 50 processes, stores and transmits/receives the signals. The functioning section 50 is provided with an internal antenna so as to transmit the bio-signals through the communication with an external controller. The functioning section 50 includes the same elements as the above-mentioned internal unit.

The electrode section 30 collects bio-signals. The electrode section 30 also functions to provide a bio-stimulating current. The internal unit is connected with the electrode section 30 so that the collected bio-signals are transferred thereto. In addition, the internal unit processes, stores and analyses the bio-signals, and transmits the bio-signals to the external part. The electrode section 30 is formed on the substrate section and may have a metal pattern-like shape.

The micro-electrode includes the substrate section 10, the cover section 20 and the electrode section 30. The micro-electrode collects bio-signals or provides bio-stimulating signals. The micro-electrode transfers the bio-signals collected by the electrode section 30 to the internal unit, receives the bio-stimulating current or signals provided from the internal unit, and applies the current or signals to a tissue in vivo through the electrode section.

The substrate section 10 provides a substrate on which the electrode section 30 is formed. The substrate section 10 also functions to insulate and protect structural elements inside the micro-electrode array package or the electrode section when the micro-electrode array package is inserted into a living body.

The cover section 20 covers the substrate section and the electrode section. The cover section 20 further includes site window holes 40 through which a portion of the electrode section is exposed to the environment in vivo. Through the window holes 40, the electrode section may be in contact with a tissue in vivo to collect bio-signals or to provide bio-stimulating current or signals. The cover section 20 also functions to insulate and protect structural elements inside the micro-electrode array package or the electrode section when the micro-electrode array package is inserted into a living body.

To perform the thermal-bonding process between the substrate section 10 and the cover section 20, a difference of melting points is used. The bonding process is carried out by heat press welding or laser welding. When adjusting the temperature in the heat press process to a temperature between the melting point of the substrate section and that of the cover section, a lower melting temperature section melts so that both sections are adhered to each other. Otherwise, when using the laser welding process, laser heating under a certain pressure causes a lower melting point section to be molten so that both sections are adhered to each other. Therefore, the cover section and the substrate section use different LCPs having different melting temperatures.

In addition, as shown in the sectional view of FIG. 3(a), the cover section 20 is formed to have a "Π"-shaped curvature, and a space is formed while the cover section and the substrate section are adhered to each other. The functioning section 50 is disposed in the space to perform its function while not being affected by the external environment. Since the functioning section 50 is disposed in the space, the micro-electrode including the electrode section, the substrate section and the cover section may be integrated with the functioning section, thereby realizing a micro-electrode array package formed as a single package type.

The functioning section 50 disposed in the space avoids a need for a feed-through as shown in the micro-electrode array package of FIG. 1. Therefore, it is possible to overcome a limitation in the number of channels. In addition, the resultant package shows excellent seal-ability since it uses single material binding instead of heterogeneous binding between a metallic or ceramic encapsulation package and a micro-electrode.

FIG. 3(b) shows a micro-electrode array package, wherein the substrate section 10 of FIG. 3(a) includes a first substrate section 11, and a second substrate section 12. As mentioned above, the tri-layer structure as shown in FIG. 3(b) may be controlled in the height (or thickness) and curvature of the micro-electrode array package. Like the micro-electrode array package as shown in FIG. 3(b), the first substrate 11 has a melting temperature different from the melting temperature of either of the second substrate section 12 and the cover section 20. The substrate sections 11 and 12 and the cover section 20 are adhered to each other with the proviso that they have different melting temperatures of the LCPs. In the micro-electrode array package as shown in FIG. 3(b), the second substrate section 12 has a lower melting temperature than the cover section 20.

FIG. 3(c) shows a micro-electrode array package, wherein the cover section 20 of FIG. 3(a) includes a first cover section 21, and a second cover section 22. The micro-electrode array package as shown in FIG. 3(c) has a tri-layer structure to control the height (or thickness) and curvature of the package and to reinforce the package shape formed on the cover section. In the micro-electrode array package as shown in FIG. 3(c), the first cover section 21 has a lower melting temperature than the substrate section 10 and the second cover section 22. Since the first cover section 21 in which the window holes 40 are formed has a lower melting temperature, a reflow phenomenon may occur during the high-temperature bonding process. Considering this, the first cover section has larger window holes as compared with the window holes of the second cover section.

FIG. 3(d) shows a micro-electrode array package, wherein the first substrate section 11 and the second substrate section 12 include electrode sections 31, 32, respectively. The tri-layer or higher structure formed in this manner allows extension of the number of electrode channels of a micro-electrode array package in the vertical direction as well as the horizontal direction. In the micro-electrode array package as shown in FIG. 3(d), the second substrate section has a lower melting temperature than the cover section and the first substrate section. Thus, a reflow phenomenon may occur during the high-temperature bonding process. Considering this, the second substrate section has larger window holes as compared with the window holes of the cover section.

Figure 4:
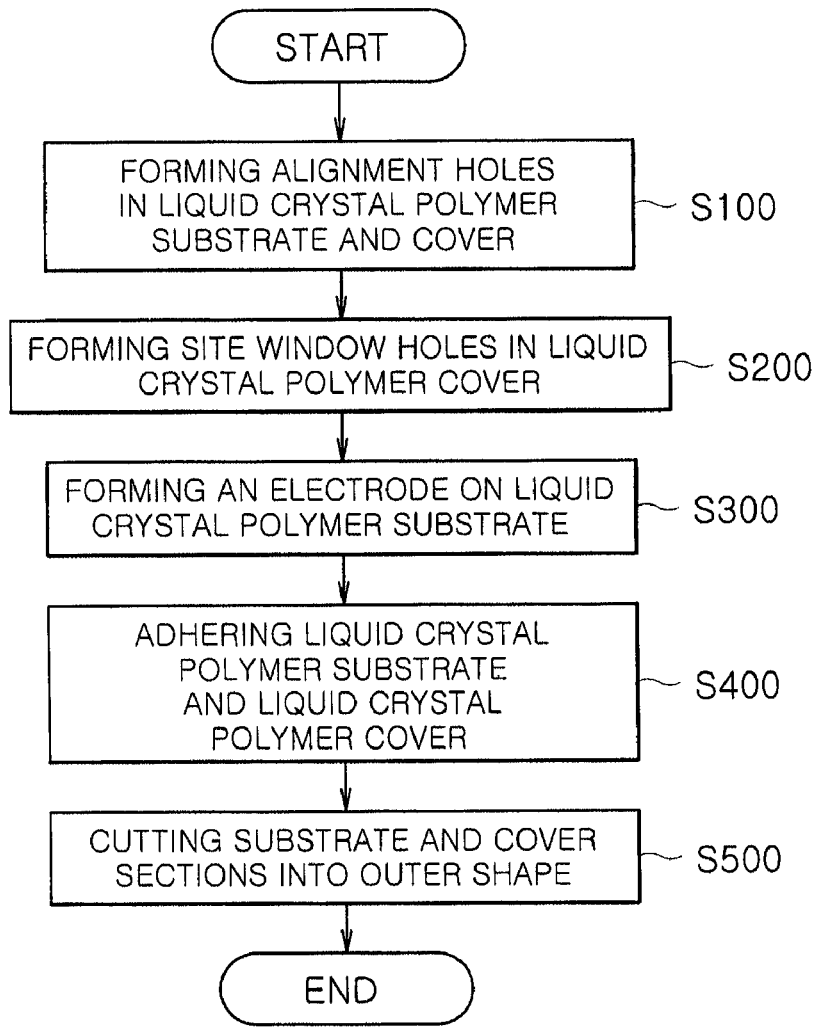
FIG. 4 is a flow chart of the method for manufacturing a micro-electrode array package according to one embodiment disclosed herein.

FIG. 4 is a flow chart of the method for manufacturing a micro-electrode array package according to one embodiment disclosed herein. The method includes: forming alignment holes in a substrate section including LCP and a cover section including LCP (S100); forming site window holes for an electrode section-exposure in the cover section (S200); forming the electrode section on one surface of the substrate section (S300); adhering the substrate section and the cover section with each other (S400); and cutting the substrate section and the cover section adhered thereto to provide an outer shape (S500).

According to one embodiment of the method for manufacturing a micro-electrode array package disclosed herein, the alignment holes which have fine key-shapes for a precise alignment process are formed on each of sections, unlike the method of the related art including formation of metal patterned alignment keys. According to the related art, the alignment keys are formed on the substrate section, the sections are assembled with each other, and then etching is performed after locating the alignment keys. However, since LCPs are opaque materials, the use of alignment keys as mentioned above prohibits one from locating the alignment keys, thereby causing misalignment.

To solve the above-mentioned problem, the method for manufacturing a micro-electrode array package using a LCP according to one embodiment includes forming alignment holes in the substrate section and the cover section, and both sections are aligned with each other using the alignment holes. The method avoids a need for a long-time plasma etching operation using an etching mask of the method according to the related art, and thus prevents such misalignment. In addition, since the method includes no plasma etching operation using an etching mask, it is possible to reduce the cost and time required for fabricating the etching mask, and to prevent each part or structure from being damaged by the etching operation.

Unlike the method according to the related art, the method for manufacturing a micro-electrode array package according to one embodiment includes forming site window holes for an electrode section-exposure before adhering the different sections are adhered to each other. Forming the window holes for an electrode section-exposure before adhering the cover section and the substrate section intends to prevent structures or metal patterns (electrode section) from being damaged by the misalignment during the etching operation. In addition, forming the window holes for an electrode section-exposure in the above-described manner intends to avoid a need for the etching mask, which, otherwise, is required for the etching operation subsequent to the thermal-bonding process according to the related art, and thus to reduce the time and cost needed for fabricating the etching mask pattern.

In other words, according to one embodiment of the method disclosed herein, the alignment holes and the window holes for an electrode section-exposure are formed before the sections forming the micro-electrode array package are adhered to each other, thereby preventing damages on the electrode and the misalignment during the etching. In addition, the method according to one embodiment of the method disclosed herein adopts a laser etching process instead of a plasma etching process, and thus avoids a need for an etching mask and reduces the time and cost required for carrying out etching.

In the operation (S100) of forming alignment holes in the substrate section including LCP and the cover section including LCP, alignment holes are formed to align the position of the holes in each layer with the position of the electrode section. The alignment holes serve to prevent misalignment of different sections during the subsequent thermal-bonding between the substrate section and the cover section, the formation of the window holes for an electrode section-exposure and the formation of the electrode section. Forming the alignment holes before the substrate section and the cover section are adhered to each other is due to the opacity of LCP. Forming alignment keys using a metal pattern as in the method according to the related art prohibits one from locating the alignment keys after the adhering the substrate section and the cover section. On the contrary, the alignment holes, which have fine key-shapes, enable precise alignment of the substrate section and the cover section and the position of the electrode section.

In the operation (S200) of forming the site window holes for an electrode section-exposure 40 in the cover section, the resultant holes 40 have size varying with the melting temperature of the LCP cover section and that of the LCP substrate section. If the cover section has a lower melting temperature than the LCP substrate section that is in contact with the bottom portion of the cover section, the window holes 40 may be formed to be larger than the desired final size. This is because the window holes may be shrunk due to a reflow phenomenon during the subsequent thermal-bonding process. On the other hand, if the cover section has a higher melting temperature than the substrate section, the window holes 40 may be formed to be the same in size as the desired final size. This is because the higher melting temperature of the cover section than the substrate section prevents the cover section from melting during the thermal-bonding process, and thus the window holes 40 formed in the cover section experiences no deformation.

In the operation (S300) of forming the electrode section on the substrate section, the electrode section is formed using conventional semiconductor based fabrication processes such as thin metal film deposition, photolithography, and wet etching or lift-off processes. In the photolithography step, a photomask for electrode patterns is aligned with aforementioned alignment holes on the substrate section, so that the electrode section can be formed on a desired position.

In the operation (S400) of adhering the substrate section and the cover section with each other, alignment pins are inserted into the alignment holes so that the substrate section and the cover section are aligned, and then both sections are adhered to each other. In this operation (S400), the substrate section and the cover section are adhered to each other using the heat press welding or laser welding. As described above, different melting temperatures of different sections enable the thermal-bonding of the sections during the heat press welding or laser welding. In other words, the bonding is accomplished by the section with a lower melting temperature.

In addition, the operation (S400) of adhering the substrate section and the cover section may further include disposing a press pad section to prevent the structure from being damaged by the pressure applied during the heat press welding or laser welding. The press pad section is disposed in such a manner that it is in contact with the surface of the substrate section having no electrode section. The press pad section has predefined 3-dimensional surface morphologies, and thus a normal pressure is applied to the convex portions of the 3-D surface, not to the concave portions thereof. The additional operation of disposing the press pad section prevents damages on the window holes for an electrode section-exposure or on the electrode section.

In the operation (S500) of cutting the substrate section and the cover section to provide an outer shape, undesired portions except the outer shape are cut out using the alignment holes. The cutting operation finishes the manufacture of a micro-electrode array package.

In addition, the operation (S100) of forming alignment holes in the substrate section including LCP and the cover section including LCP, the operation (S200) of forming the site window holes for an electrode section-exposure in the cover section, and the operation (S500) of cutting the substrate section and the cover section to provide an outer shape may be carried out by laser processing. The adoption of laser processing results from the fact that plasma processing used in the related art provides a low etching rate and increased exposure time of the electrode section, leading to damages on the electrode section and non-uniform etched surfaces and appearances.

Figure 5:
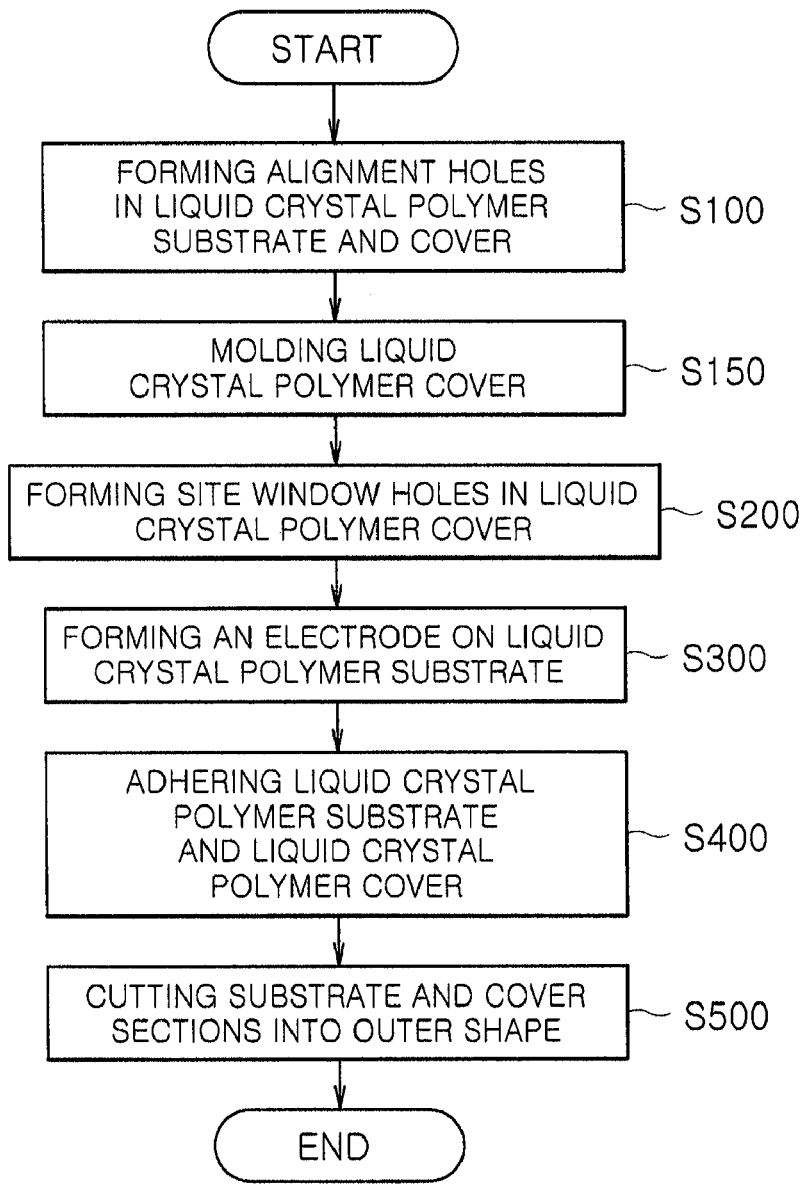
FIG. 5 is a flow chart of the method for manufacturing a micro-electrode array package according to another embodiment disclosed herein.

FIG. 5 is a flow chart of the method for manufacturing a micro-electrode array package according to another embodiment disclosed herein. The method includes: forming alignment holes in a substrate section including LCP and a cover section including LCP (S100); molding the cover section (S150); forming site window holes for an electrode section-exposure on the cover section (S200); forming the electrode section on one surface of the substrate section (S300); adhering the substrate section and the cover section with each other (S400); and cutting the substrate section and the cover section adhered thereto to provide an outer shape (S500).

In other words, the flow chart of FIG. 5 is similar to that of FIG. 4, except that the former further includes molding (S150) the cover section right after forming (S100) the alignment holes. The operation of molding the cover section secures a space between the cover section and the substrate section. The space is independent from the external environment. For example, the space is not in contact with moisture or ions in vivo. Additionally, the operation (S150) of molding the cover section may include molding the cover section by heat press processing. A mold conformed to the size of the space is provided, and then the substrate section is introduced into the mold, followed by pressurizing and heating, to obtain the cover section molded in a desired shape.

Referring to FIG. 1, a separate encapsulated package is required to install the internal unit according to the related art. The encapsulated package includes a metal or ceramic material. In other words, the encapsulated package is formed from a material different from the micro-electrode section. Therefore, as shown in FIG. 1, a feed-through is used to bind the encapsulated package to the micro-electrode section, resulting in degradation of the sealability and a limitation in the number of channels.

On the contrary, molding the cover section as shown in (S150) of FIG. 5 provides a space formed of a single LCP material and the internal unit is disposed in the space. In other words, a single package surrounded with the substrate section and the cover section is provided, thereby realizing improved sealability. In addition, use of a feed-through is avoided, and thus the electrode section may be formed to have a high-density multi-channel structure without limitations related to the number of feed-through channels. In other words, it is possible to realize a micro-electrode array package using a single material, thereby solving the problems occurring in the related art.

The example embodiments of the method for manufacturing a micro-electrode array package disclosed herein will now be described. Each embodiment may be realized to have a different thickness of a micro-electrode array package. The following example embodiments are for illustrative purposes only and not intended to limit the scope of this disclosure.

Figure 6:
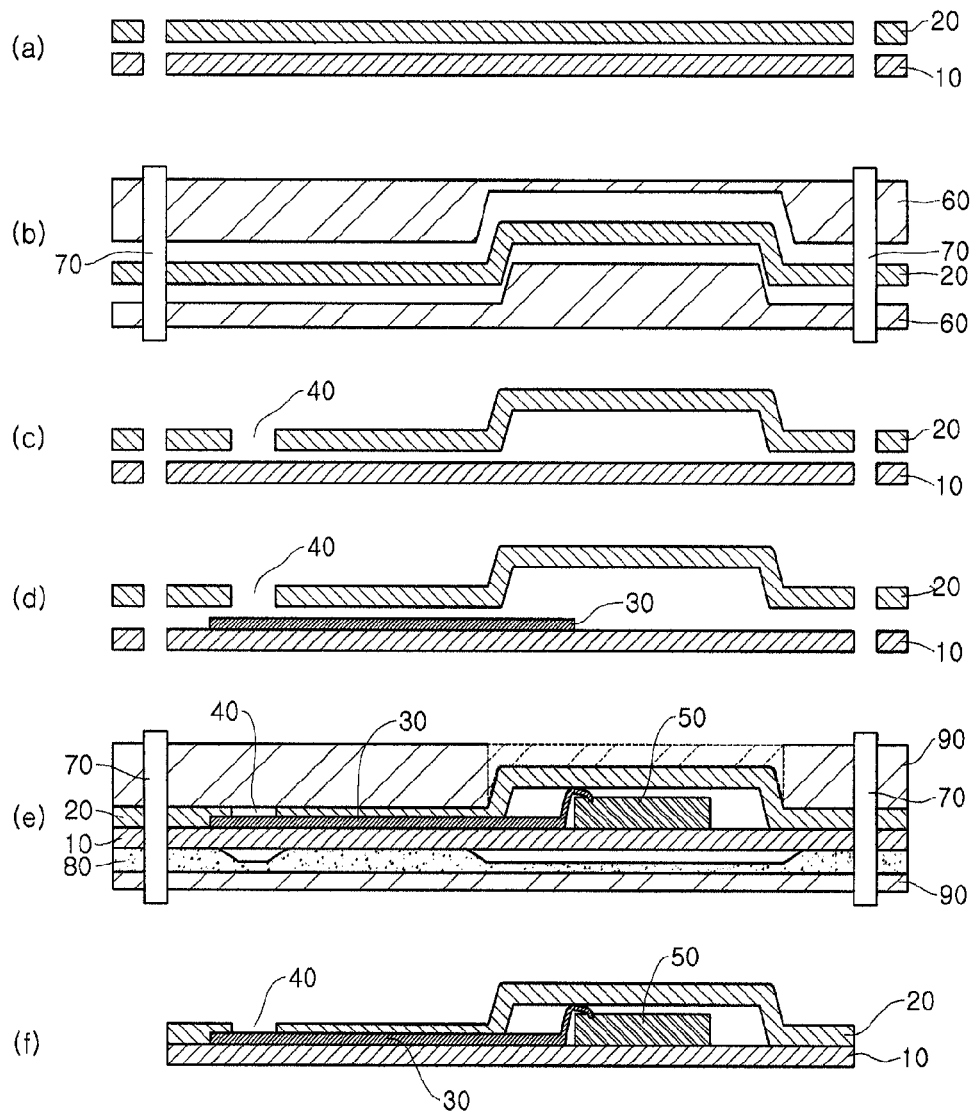
FIG. 6 illustrates the method for manufacturing a micro-electrode array package according to one embodiment disclosed herein.

FIG. 6 illustrates the method for manufacturing a micro-electrode array package according to one embodiment disclosed herein. In the embodiment as shown in FIG. 6, a micro-electrode array package is manufactured using two LCP layers. In the operation as shown in FIG. 6(a), alignment holes are formed in a substrate section including LCP and a cover section including LCP. Upon the thermal-bonding of the substrate section and that of the cover section, both sections are aligned by the alignment holes. The alignment holes are formed by laser processing.

In the operation as shown in FIG. 6(b), the cover section is molded using a mold 60. During the molding operation, alignment pins 70 are inserted into the alignment holes to prevent displacement of the alignment holes. The cover section is molded to provide a "Π"-shaped curvature, thereby forming a space upon the bonding between the cover section and the substrate section. In the operation as shown in FIG. 6(c), site window holes for an electrode section-exposure 40 are formed in the molded cover section. The window holes 40 function as a pathway through which bio-signals are collected. The window holes 40 are formed by laser processing. In the operation as shown in FIG. 6(d), an electrode section 30 is formed on the substrate section. The electrode section 30 transfers the bio-signals to an internal unit. The signal sensitivity varies with the exposure degree of the electrode section.

In the operation as shown in FIG. 6(e), the internal unit is disposed and assembled in the space, and the substrate section and the cover section are adhered to each other by heat press welding or laser welding. The press mold 90 is designed to provide an empty space to the portion having the internal unit (i.e., the portion having a "Π"-shaped curvature), as shown by the dotted line, in order to prevent electronic devices and batteries susceptible to heat from being heated during the thermal-bonding process. The window holes for an electrode section-exposure 40 or the electrode section may be damaged, when the window holes 40 and the portion having the space are subjected to an excessive pressure. Thus, an additional press pad section 80 is provided to prevent such damages on the window holes 40 or the electrode section. After the press pad section 80 is allowed to be in contact with one surface of the substrate section having no electrode section, the press mold 90 is mounted in place, and then the heat press welding or laser welding is carried out. To prevent misalignment of the window holes 40 and the electrode section, the alignment pins 70 are inserted into the alignment holes before the pressurization and heating. FIG. 6(f) shows a finished micro-electrode array package.

The method for manufacturing a micro-electrode array package with a tri-layer structure as shown in FIG. 3(b) may be carried out using the process as shown in FIG. 6. In this case, since the substrate section includes the first substrate section and the second substrate section, alignment holes are formed at the three sections ($1^{st}$ substrate, $2^{nd}$ substrate and cover) in the operation as shown in FIG. 6(a). Then, in the operation as shown in FIG. 6(e), the two substrate sections are introduced into the mold instead of one substrate section, followed by heat press welding or laser welding.

The method for manufacturing a micro-electrode array package with a tri-layer structure as shown in FIG. 3(c) may also be carried out using the process as shown in FIG. 6. In this case, since the cover section includes the first cover section and the second cover section, alignment holes are formed at the three sections (substrate, $1^{st}$ cover and $2^{nd}$ cover) in the operation as shown in FIG. 6(a). In addition, the two cover sections are molded in the operation as shown in FIG. 6(b), and then site window holes for an electrode section-exposure are formed on the two cover sections in the operation as shown in FIG. 6(c). Then, in the operation as shown in FIG. 6(e), the two cover sections are introduced into the mold instead of one cover section, followed by heat press welding or laser welding.

Meanwhile, in the case of the method for manufacturing a micro-electrode array package with a tri-layer structure as shown in FIG. 3(d), each of the first substrate section and the second substrate section includes an electrode section respectively. Thus, alignment holes are formed at three sections ($1^{st}$ substrate, $2^{nd}$ substrate and cover) in the operation as shown in FIG. 6(a). In addition, additional site window holes for an electrode section-exposure are formed on the second substrate section in the operation as shown in FIG. 6(c), and then each electrode section is formed on the first substrate section and the second substrate section in the operation as shown in FIG. 6(d). Then, in the operation as shown in FIG. 6(e), the internal unit is assembled with the two substrate sections, followed by heat press welding or laser welding.

Figure 7:
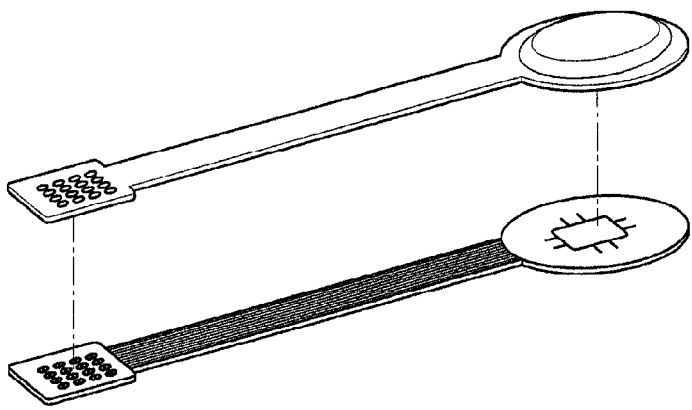
FIG. 7 is a perspective view of the micro-electrode array package according to one embodiment disclosed herein.

FIG. 7 is a perspective view of the micro-electrode array package according to one embodiment disclosed herein. Unlike the conventional micro-electrode array package as shown in FIG. 1, the micro-electrode array package as shown in FIG. 7 has a single package. In FIG. 7, the micro-electrode array package is shown in two portions, wherein the upper portion shows the cover section described hereinbefore and the lower portion shows the substrate section including the electrode section and the functioning section. As can be seen from FIG. 7, the micro-electrode array package disclosed herein is significantly different from the conventional micro-electrode array package.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A method for manufacturing a micro-electrode array package using a liquid crystal polymer, comprising:
   forming alignment holes in a substrate section including a first liquid crystal polymer and in a cover section including a second liquid crystal polymer;
   molding the cover section to form a curved shape;
   forming site window holes for an electrode section-exposure in the cover section;

forming an electrode section on a surface of the substrate section, the electrode section extending along at least a portion of the surface of the substrate section;

aligning the substrate section and the cover section using the alignment holes, and adhering the substrate section and the cover section with each other; and cutting the substrate section and the cover section adhered thereto to provide an outer shape.

2. The method for manufacturing a micro-electrode array package according to claim 1, wherein forming the alignment holes, forming the site window holes for the electrode section-exposure, adhering the substrate section and the cover section, and cutting the substrate section and the cover section to provide the outer shape are carried out by laser processing.

3. The method for manufacturing a micro-electrode array package according to claim 1, wherein the cover section has a higher melting temperature than the substrate section and the cover section and the substrate section are adhered to each other by the difference between the melting temperature of the substrate section and the melting temperature of the cover section.

4. The method for manufacturing a micro-electrode array package according to claim 1, wherein the molded cover section secures a space independent from the external environment between the cover section and the substrate section.

5. The method for manufacturing a micro-electrode array package according to claim 4, wherein molding the cover section includes molding the cover section by heat press processing.

6. The method for manufacturing a micro-electrode array package according to claim 4, which further comprises disposing a functioning section for generating/processing signals and transmitting/receiving signals in the space, so that the functioning section is not affected by the external environment.

7. The method for manufacturing a micro-electrode array package according to claim 1, wherein adhering the substrate section and the cover section with each other includes disposing a press pad section in contact with another surface of the substrate section having no electrode section.

8. The method for manufacturing a micro-electrode array package according to claim 7, wherein the press pad section has 3-dimensional surface morphology so that different amounts of pressures are applied to different positions of the substrate sections during a thermal-bonding process.

* * * * *